United States Patent [19]
Chen et al.

[11] Patent Number: 6,066,132
[45] Date of Patent: May 23, 2000

[54] ARTICULATING ENDOMETRIAL ABLATION DEVICE

[75] Inventors: Chao Chen, Edison; E. Richard Skula, Wayne, both of N.J.

[73] Assignee: Ethicon, Inc., Somerville, N.J.

[21] Appl. No.: 09/107,631

[22] Filed: Jun. 30, 1998

[51] Int. Cl.[7] .................................................. A61B 18/04
[52] U.S. Cl. .......................... 606/28; 606/21; 607/105; 607/113; 604/530
[58] Field of Search .................... 606/27, 28, 192, 606/193, 20–23; 607/96, 100, 101, 104, 105, 113, 114; 604/264, 530; 600/585, 143, 146, 151

[56] References Cited

U.S. PATENT DOCUMENTS

| | | | |
|---|---|---|---|
| 2,077,453 | 4/1937 | Albright | 128/254 |
| 2,190,384 | 2/1940 | Newman | 128/400 |
| 3,924,628 | 12/1975 | Droegemueller et al. | 128/303.1 |
| 4,709,698 | 12/1987 | Johnston et al. . | |
| 4,754,752 | 7/1988 | Ginsburg et al. . | |
| 4,813,425 | 3/1989 | Malis . | |
| 4,836,208 | 6/1989 | Ulbrich . | |
| 4,865,029 | 9/1989 | Pankratov et al. | 606/4 |
| 4,949,718 | 8/1990 | Neuwirth et al. . | |
| 4,979,948 | 12/1990 | Geddes et al. . | |
| 5,045,056 | 9/1991 | Behl . | |
| 5,084,044 | 1/1992 | Quint . | |
| 5,100,388 | 3/1992 | Behl et al. . | |
| 5,105,808 | 4/1992 | Neuwirth et al. . | |
| 5,159,925 | 11/1992 | Neuwirth et al. . | |
| 5,191,883 | 3/1993 | Lennox et al. . | |
| 5,195,965 | 3/1993 | Shantha . | |
| 5,222,938 | 6/1993 | Behl . | |
| 5,242,390 | 9/1993 | Goldrath . | |
| 5,257,977 | 11/1993 | Eshel . | |
| 5,277,201 | 1/1994 | Stern . | |
| 5,433,708 | 7/1995 | Nichols et al. . | |
| 5,437,629 | 8/1995 | Goldrath . | |
| 5,445,470 | 8/1995 | Schirtzinger . | |
| 5,449,380 | 9/1995 | Chin . | |
| 5,451,208 | 9/1995 | Goldrath . | |
| 5,460,628 | 10/1995 | Neuwirth et al. . | |
| 5,478,330 | 12/1995 | Imran et al. | 604/282 |
| 5,492,529 | 2/1996 | Neuwirth et al. . | |
| 5,501,681 | 3/1996 | Neuwirth et al. . | |
| 5,503,626 | 4/1996 | Goldrath . | |
| 5,505,730 | 4/1996 | Edwards . | |
| 5,540,658 | 7/1996 | Evans et al. . | |
| 5,542,928 | 8/1996 | Evans et al. . | |
| 5,558,672 | 9/1996 | Edwards et al. . | |
| 5,562,720 | 10/1996 | Stern et al. . | |
| 5,569,210 | 10/1996 | Moen . | |
| 5,571,153 | 11/1996 | Wallsten . | |
| 5,575,772 | 11/1996 | Lennox . | |
| 5,575,788 | 11/1996 | Baker et al. . | |
| 5,645,561 | 7/1997 | Smith et al. | 606/193 |
| 5,653,692 | 8/1997 | Masterson et al. . | |
| 5,704,934 | 1/1998 | Neuwirth et al. . | |
| 5,800,493 | 9/1998 | Stevens . | |
| 5,827,269 | 10/1998 | Saadat | 606/28 |
| 5,891,134 | 4/1999 | Goble et al. | 606/27 |
| 5,916,213 | 6/1999 | Haissaguerre et al. | 606/41 |

FOREIGN PATENT DOCUMENTS

| | | | |
|---|---|---|---|
| 0 672 402 A1 | 9/1995 | European Pat. Off. | A61F 13/15 |
| 0 449 472 B1 | 12/1995 | European Pat. Off. | A61F 7/12 |
| WO 94/21202 | 9/1994 | WIPO | A61F 7/12 |
| WO 94/21203 | 9/1994 | WIPO | A61F 7/12 |
| WO 96/15740 | 5/1996 | WIPO | A61F 7/12 |
| WO 96/15741 | 5/1996 | WIPO | A61F 7/12 |
| WO 96/26695 | 9/1996 | WIPO | A61F 7/12 |
| WO 96/33664 | 10/1996 | WIPO | A61B 17/38 |

*Primary Examiner*—Linda C. M. Dvorak
*Assistant Examiner*—David M. Ruddy
*Attorney, Agent, or Firm*—Verne E. Kreger

[57] ABSTRACT

An intrauterine ablation device having a catheter, a handle, and a distensible bladder. The catheter contains a joint such that the catheter may be articulated to facilitate access into the uterus.

4 Claims, 7 Drawing Sheets

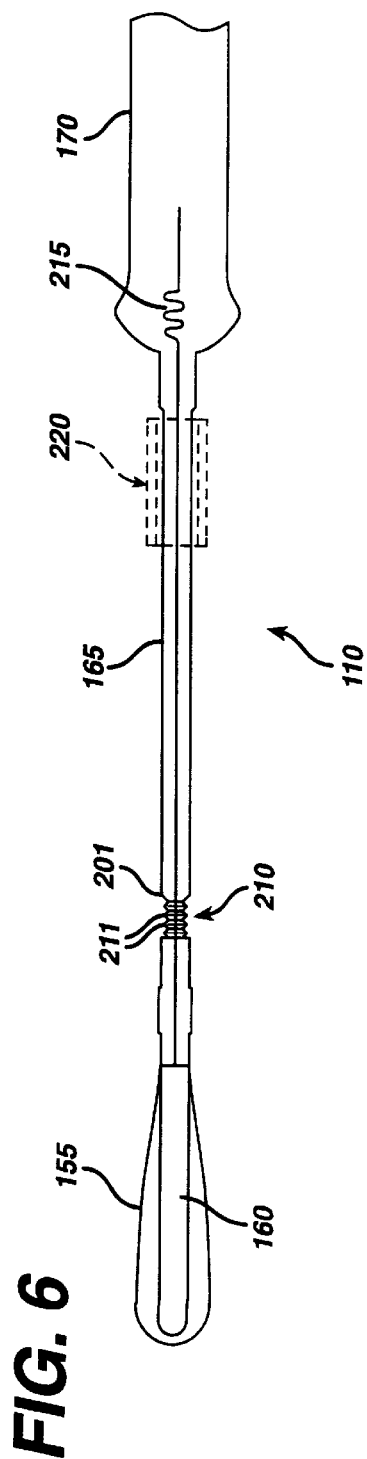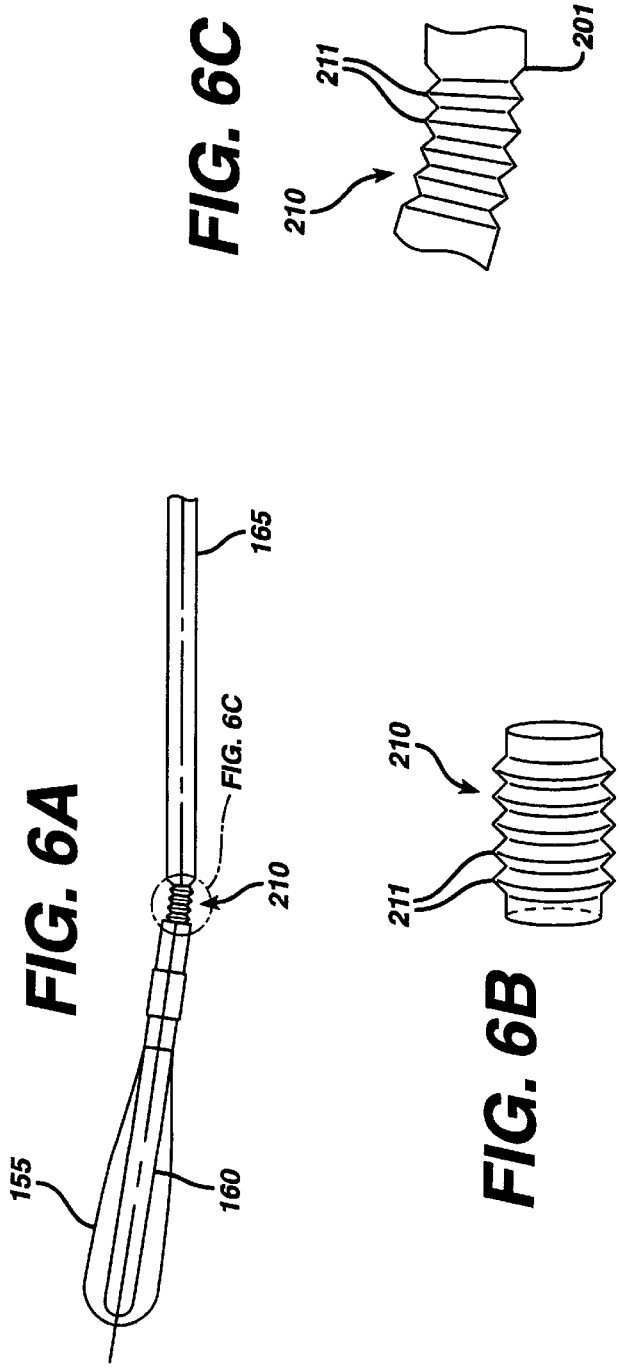

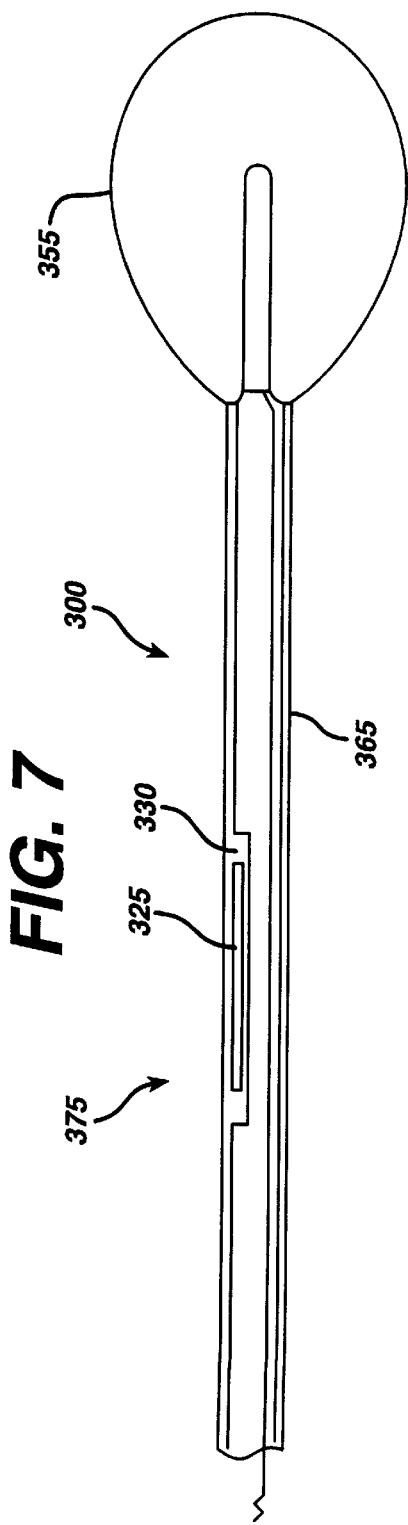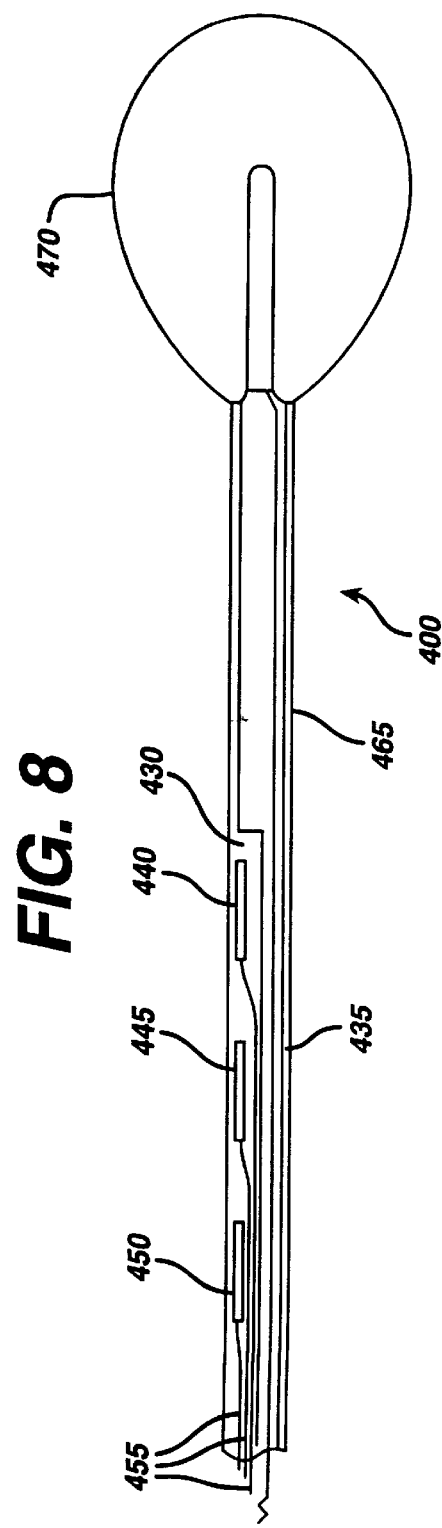

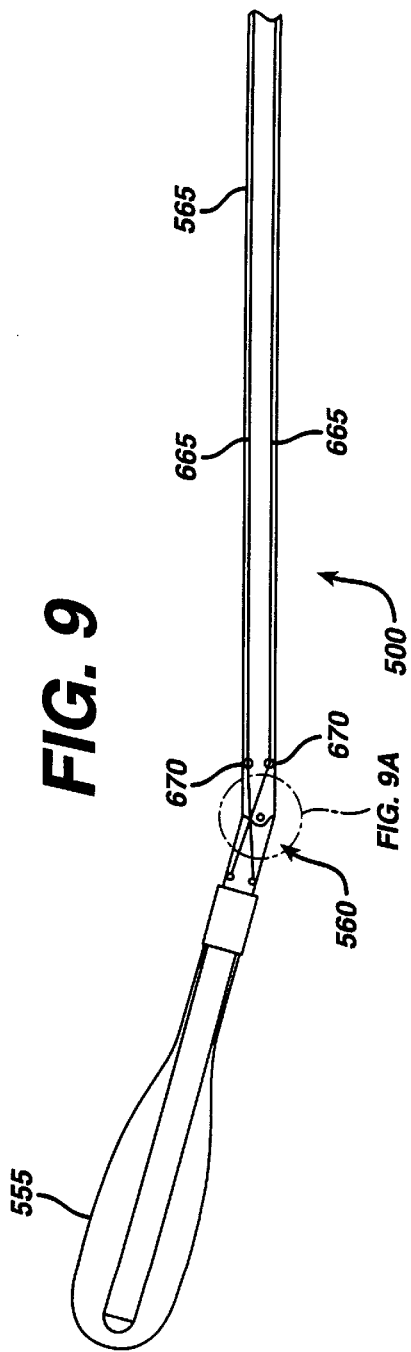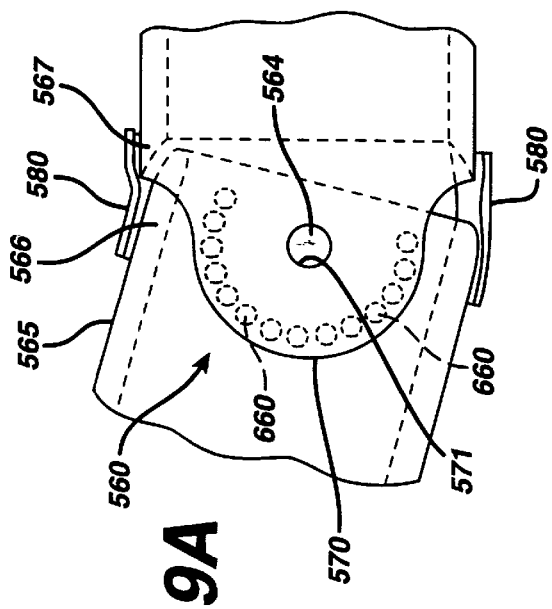

US 6,066,132

ARTICULATING ENDOMETRIAL ABLATION DEVICE

FIELD OF THE INVENTION

This invention relates to medical devices for ablating tissue, more particularly to a balloon ablation device for ablating endometrial tissue.

BACKGROUND OF THE INVENTION

Menorrhagia is a medical condition in women which manifests symptoms including excessive and difficult to control bleeding of the endometrial layer of the uterus. The endometrium is usually thought of as the inner lining of the uterus to which an embryo normally attaches and, typically excludes the portion of the uterine inner lining forming the cervix. The symptoms of menorrhagia are believed to be experienced by a significant segment of the female population. Accordingly, a number of treatments have been developed over the years to remediate this condition. One radical procedure, i.e., hysterectomy, requires the complete surgical removal of the uterus. This surgical procedure has been the treatment of choice in the past and continues to be the ultimate solution if this condition is otherwise non-responsive. Because of the extremity and seriousness of this operation, both, in terms of physical and mental effects, attempts have been made to develop less invasive, less radical approaches to relieving menorrhagia.

These less invasive approaches have been typically directed at inducing necrosis of the endometrial layer and a portion of the myometrial layer. Known procedures include, inter alia, mechanically scraping the endometrial surface, freezing of the endometrial layer cryogenically, cauterizing the endometrial layer of the uterus by means of a laser hysteroscope, treating the uterus with microwave generated heat, and ablating the endometrial tissue with an electrosurgical probe. In addition, another known technique involves necrotizing the endometrial tissue by the application heat, for example, using a liquid filled expandable balloon or directly contacting the endometrium with hot liquid.

The existing cryogenic methods typically require a device having a probe or an extendable bladder which is inserted into the uterus and filled with a circulating gas or fluid at cryogenic temperatures. The cryogenic coolant is typically liquid nitrogen or Freon which is maintained at a sufficient pressure to expand the bladder into close contact with the endometrium. Such a procedure is disclosed in U.S. Pat. No. 3,924,628.

Other known endometrial ablation procedures involve the use of laser devices; these devices require considerable skill by the surgeon. A relatively narrow laser beam must be moved so as to cover the whole surface of the endometrium, which may be rather tedious and time consuming. Additionally, care must be taken to apply the appropriate dosage of radiation. If the dosage is too low, the treatment may be incomplete and bleeding may recur, if too high, the laser may burn too deeply into the uterus or even perforate it.

Another technique involves heating the endometrium with microwaves. This technique has proven to be complex and possibly unreliable because of the irregular shape of the uterus, which makes even energy distribution difficult. The large flow of blood from the endometrium may result in temperature drops due to the cooling effect of the blood. The cooling effects need to be compensated for in order to prevent uneven heating.

Another known treatment technique utilizes a balloon and heated liquid. The balloon is mounted to the distal end of a catheter that is inserted into the patient's uterus. The balloon is inflated with a liquid, such that the walls of the balloon are substantially in intimate contact with the endometrial layer of the uterus. The liquid is then heated to an elevated temperature so as to cause necrosis and ablation of the cells on the endometrial surface. The liquid may also be heated prior to inflation of the balloon Fluids, such as heated water are utilized as a heating means. U.S. Pat. No. 5,084,044 describes a method for the ablation of tissue in which a distensible balloon, affixed to the end of a catheter, is inserted into a body cavity and inflated using a source of externally heated liquid. This requires that at least part of the catheter be well insulated so as not to burn adjacent healthy tissue for example in the cervix or the vagina.

U.S. Pat. No. 4,949,718 discloses an apparatus for effecting necrosis of a tissue lining of a body cavity, specifically the uterine endometrium, by introducing a distensible bladder connected to a catheter into the uterus. The bladder is expanded by introducing a non-toxic, biocompatible fluid under pressure, heating the fluid in the bladder by means located internal to the bladder and controlling the pressure of the fluid and its temperature. U.S. Pat. No. 5,105,808 discloses a method of using this apparatus to effect cauterization necrosis of the uterine endometrium and other body cavities. U.S. Pat. No. 5,460,628 discloses a balloon treatment apparatus with a means for agitating the fluid within the extended balloon in order to better control the heat to which the endometrium is exposed. International Publication No. WO 96/33664 describes a similar apparatus for endometrial ablation and, in particular, describes the heating element within the extendable bladder. U.S. Pat. No. 5,571,153 discloses a balloon and catheter treatment apparatus.

Although the balloon catheter devices having internal heaters are safe and effective for their intended use ( i.e., primarily endometrial ablation), there may be some potential advantages associated with placing the heating element outside of the balloon bladder. Since there is a variation in size and, to some extent, in shape of the human uterus it would be preferable to make available devices with differently sized and shaped expandable balloons. The balloon material must be both expandable and sufficiently rugged so as to be able to exert the desired pressure on the endometrial tissue on all of the walls of the irregularly shaped uterus so as to effect intimate contact with said tissue. If the bladder is too small, it may not be able to contact all of the walls at its full extension. Conversely, if it is too large for the uterus, it may not be able to make intimate contact in all areas of the endometrium because of folds which might be present on the balloon if it has not been fully extended.

U.S. Pat. No. 5,653,692 discloses an endometrial ablation device in which heated fluid contacts the endometrial layer directly. The fluid is introduced at about room temperature and is heated within the uterus by means of electrodes which release RF energy. The fluid is agitated with an impeller located within the uterus itself This may appear to resolve the problem of differently sized uteri but, actually, introduces a number of other difficulties, e.g., undesirable influx into the fallopian tubes.

The inflatable balloon devices, described above, have the balloon permanently affixed to a catheter which has passages that supply the fluid for the expansion of the balloon. The passages also supply the energy source for heating the fluid and the feedback devices which allow for control of the various functions needed to successfully expand the balloon and heat and agitate the fluid within the balloon.

The devices of the past have all been based on having the balloon or bladder attached to the distal end of a relatively stiff catheter in order to enable its insertion through the vagina and cervix into the uterus. However, the uterine opening and the uterus itself are not normally completely aligned with the vagina to enable easy insertion of the device. Furthermore the vagina is frequently found in retroflexed or anteflexed positions within the body. At times, this has made the insertion of these ablation devices difficult and uncomfortable.

All of the thermal ablation devices discussed above are designed to be substantially straight instruments which are inserted into the vagina and from there into the uterus. In a standing woman the vagina and the uterus are, from a frontal view, in line with each other. From a side view, however, the uterus normally forms an acute angle with the vagina. When the woman is in a supine position, the uterus tends to drop backward, more in line with the vagina. This effect can be even greater when the patient is placed on an operating table such that the pelvis is elevated. Even with this elevation of the pelvis, the transition from the vagina to the uterus is seldom in a straight line. Thus, the opening into the uterus has to be probed for, causing potential damage to the patient's tissue and frustration to the physician. Various degrees of retroflexion and anteflexion of the uterus are not uncommon and contribute even more to the difficulties encountered when the physician attempts to place the ablator into the uterus without undue comfort or even damage to the tissues of the vagina or uterus.

Accordingly, there is a need in this art for improved uterine catheter balloon devices.

SUMMARY OF THE INVENTION

It is an object of the present invention to facilitate the placement of an endometrial ablating device into the uterus while minimizing any potential damage to tissues.

It is a further object of the present invention to provide an endometrial ablation device having the ability to articulate the heretofore straight catheter used to introduce the ablation device into the uterus. After an evaluation of the position of the uterus relative to the vagina in the individual patient, the physician can then bend the catheter at the point where articulation has been made possible. Because the vagina is capable of a high degree of deformation a bent instrument is easily inserted. Alternately, in some embodiments of this invention, he can bend the catheter as he enters the uterus.

Accordingly, a novel uterine balloon catheter apparatus is disclosed. The uterine balloon treatment apparatus has a catheter having a longitudinal internal passage or lumen, a distal end and a proximal end. An inflatable balloon is mounted to the distal end of the catheter. The inflatable balloon has an interior, wherein the interior of the inflatable member is in fluid communication with the internal lumen of the catheter. A hollow cylindrical handle is mounted to the proximal end of the catheter. A connector is mounted to the handle for connecting internal lumen of the catheter to a source of liquid. A heating element mounted in the interior lumen of the catheter such that when said heating element is connected to a source of electrical power it generates heat. Electrical conductors are provided for conducting electrical power to the heating element. The catheter has a joint located between the proximal and distal ends which allows the catheter to be articulated.

Yet another aspect of the present invention is a uterine ablation device as described above but having a cryogenic cooling element in the balloon.

Yet another aspect of the present invention is a method of ablating endometrial tissue using the above-described articulating apparatus.

These and other advantages of the present invention will become more apparent by the following description and accompanying drawings.

BRIEF DESCRIPTION OF THE DRAWINGS

FIG. 6 illustrates a top view of an embodiment of the catheter portion of an endometrial ablation device of the present invention.

FIG. 6A is a partial top view of the catheter of FIG. 6 showing the catheter in an articulated, angulated position.

FIG. 6B is a partial magnified view of the articulating joint of the catheter of FIG. 6.

FIG. 6C is an exploded view of the joint shown in FIG. 6A.

FIG. 7 shows the catheter portion of an endometrial ablation device in accordance with another embodiment of the present invention.

FIG. 8 illustrates the catheter portion of an alternate embodiment of the endometrial ablation device of the present invention.

FIG. 9 illustrates the catheter portion of an additional embodiment of the endometrial ablation of the present invention.

FIG. 9A is an exploded view of the joint shown in FIG. 9.

DETAILED DESCRIPTION OF THE PREFERRED EMBODIMENTS

The disclosures of U.S. Pat. Nos. 4,949,718 and 5,105, 808 and 5,460,628 and 5,501,681 are incorporated by reference.

Figure 1:
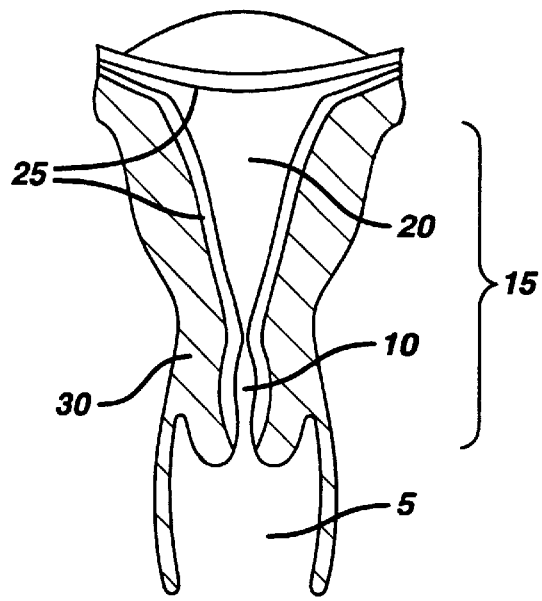
FIG. 1 is a diagram of the relative positions of the vagina and the uterus as they are in an erect woman viewed from the front.
Figure 2:
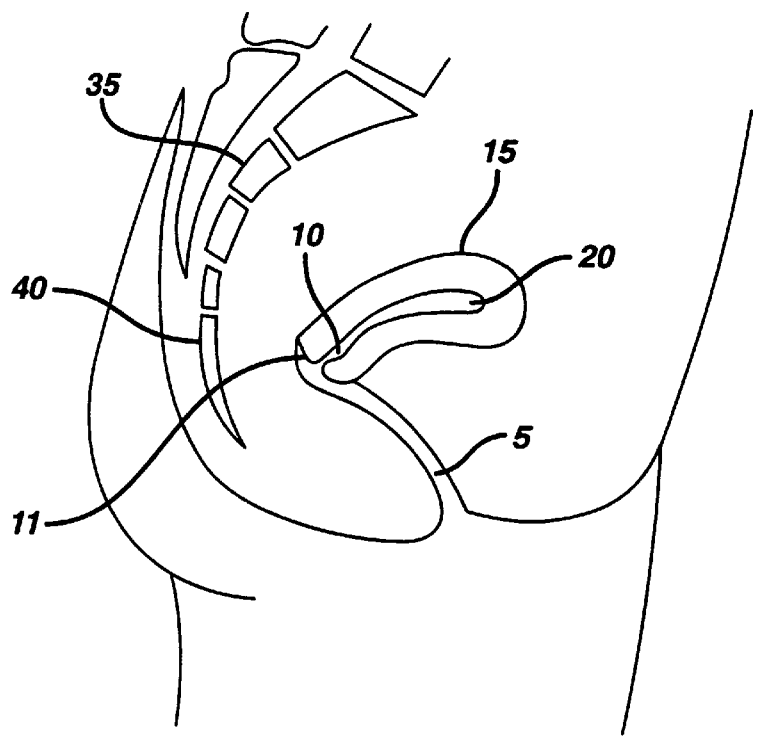
FIG. 2 is a diagram of the relative positions of the vagina and the uterus as they are in an erect woman viewed from the side.
Figure 3A:
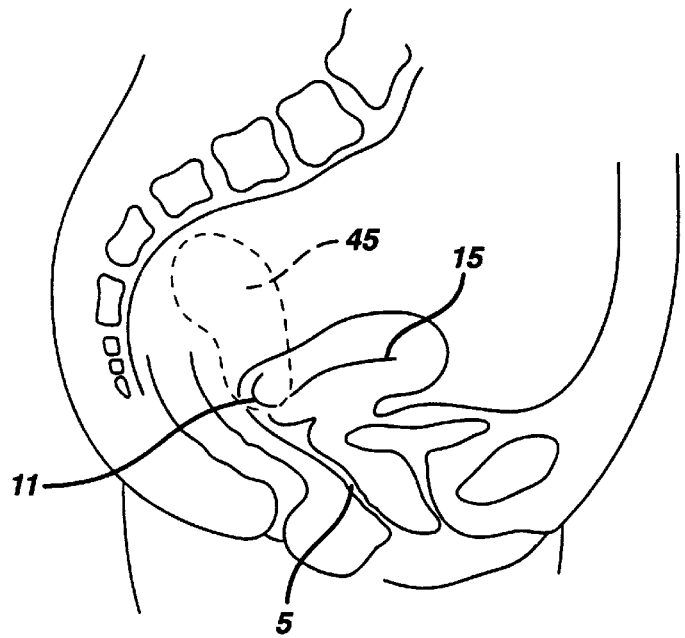
FIG. 3 is a diagram of the relative positions of the vagina and the uterus as they are in an erect woman viewed from the side. The uterus is also superimposed in retroflexion and in anteflexion.
Figure 3B:
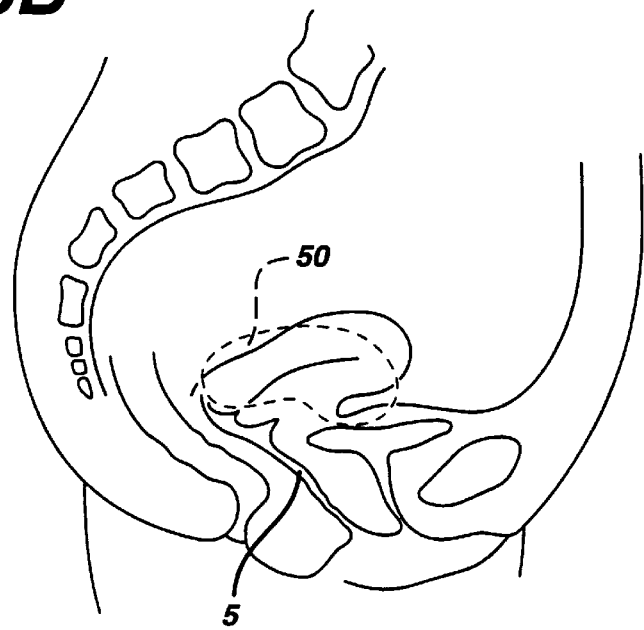
Figure 4:
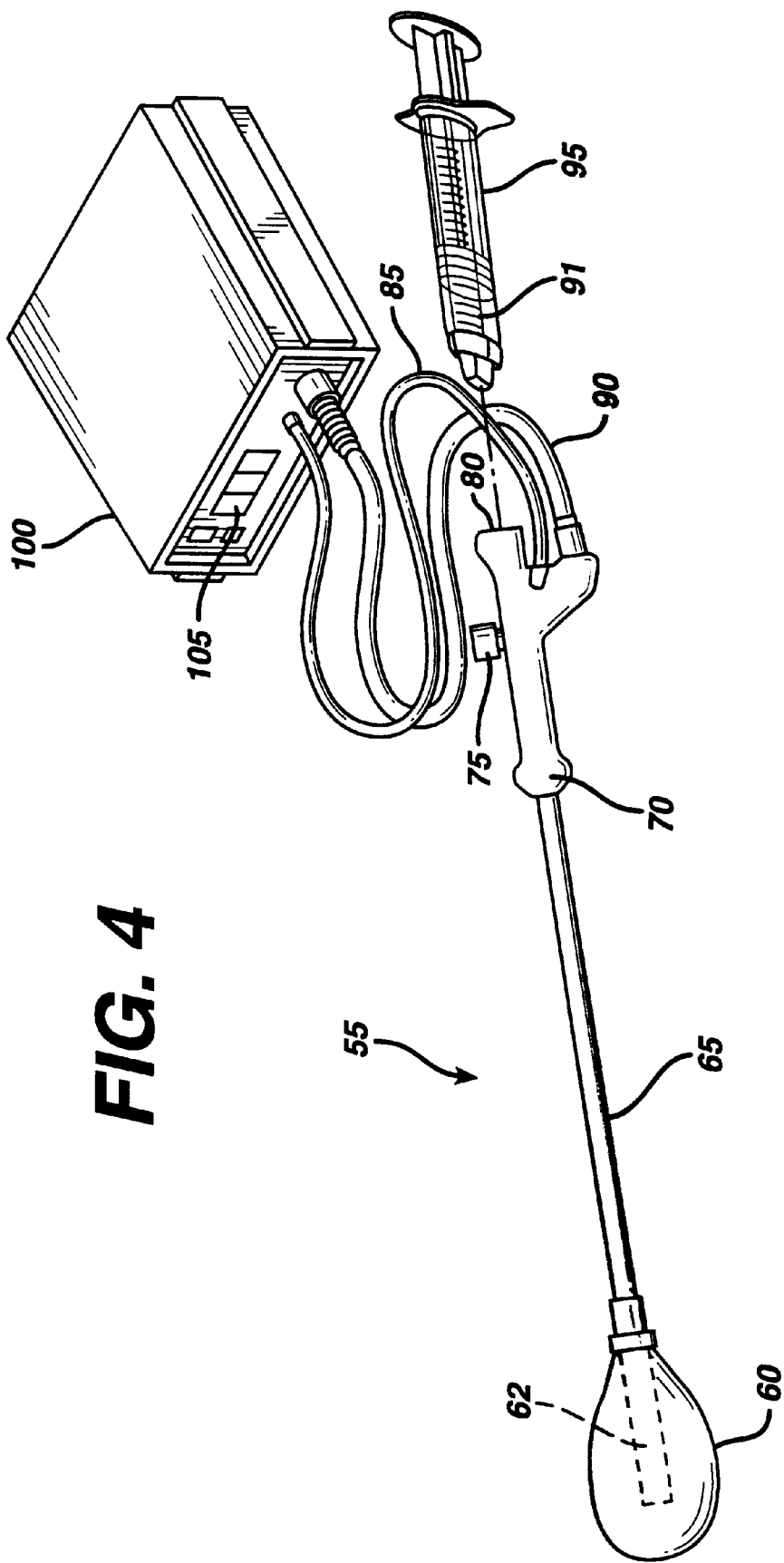
FIG. 4 illustrates an endometrial ablation device as described in the prior art.

In discussing the drawings in greater detail, reference numerals designate like or corresponding elements among the several views. FIG. 1 shows an outline of the relative positions of the vagina and the uterus as they are normally placed in an erect woman viewed from the front. The vagina 5 meets the cervix 10 of the uterus 15 in substantially straight alignment. The cervix 10 leads directly to the uterine cavity 20, and is part of the uterus 15. The interior of the uterus 10 is lined with the endometrium 25. In treating excessive bleeding, it is the endometrial layer 25 that has to be necrosed. This is preferably done without damage to the myometrium 30 which is the layer of cells adjacent to and below the endometrium 25. As seen in FIG. 2, there is an outline of the normal relative positions of the vagina 5 and the uterus 10 as they are in an erect woman viewed from the side. The sacrum 35 and coccyx 40, both portions of the backbone are shown to orient the viewer. The vagina 5 is seen to meet the cervix 10 at junction 11 at an acute angle. It can be seen that introducing a conventional straight medical instrument into the uterus 15 requires substantial manipulation. The instrument has to be able to navigate around the angle at junction 11 or some other way to reduce this angle has to be found. FIG. 3 presents a sagittal view of the relative positions of the vagina 5 and the uterus 15 as in FIG. 2, but adds two alternate positions, 45 and 50, for the uterus. When the uterus is in the position shown at 45, it is said to be in retroflexion and when it is in position 50, it is said to be in anteflexion. While the retroflex position diminishes the angle formed where the vagina 5 and the uterus 10 meet at junction 11, the anteflex position increases the acuteness of the angle between the vagina 5 and the uterus 10. Both of these positions, to one degree or another, are not uncommon. This variation from the norm increases the difficulty of instrument insertion for the surgeon. FIG. 4 shows an endometrial ablation device 55 in accordance with the prior art. The bladder 60 with the internal heater 62 is at the distal end of the insertion catheter 65. The terms bladder and balloon are used interchangeably herein. The catheter is connected to a handle 70 which contains a valve 75, a liquid insertion port 80, a liquid pressure readout lead 85 and a connector for the power supply and temperature readout and control leads 90. Liquid is manually pressured into the bladder 60 using a syringe 95. Both, the liquid pressure readout lead 85 and the power feed and temperature control leads 90 are hooked to the control box 100. Pressure and temperature information, as well as other data that may be desirable to display, are shown in the various displays 105. It can be seen that the conventional insertion catheters 65 of the prior art are typically straight and rigid or semi-rigid and therefore may require substantial manipulation to insert. An alternate embodiment of the present invention uses a cryogenic cooing element mounted within the balloon, rather than a heating element. The balloon may be first inflated with a fluid (liquid or gas) in contact with the cryogenic element which conducts heat from the endometrium for a sufficient amount of time to effectively ablate the tissue, as disclosed in U.S. Pat. No. 5,501,681 which is incorporated by reference. The cryogenic element may be connected to a conventional cryogenic refrigeration system or a conventional source of liquefied gas.

Figure 5:
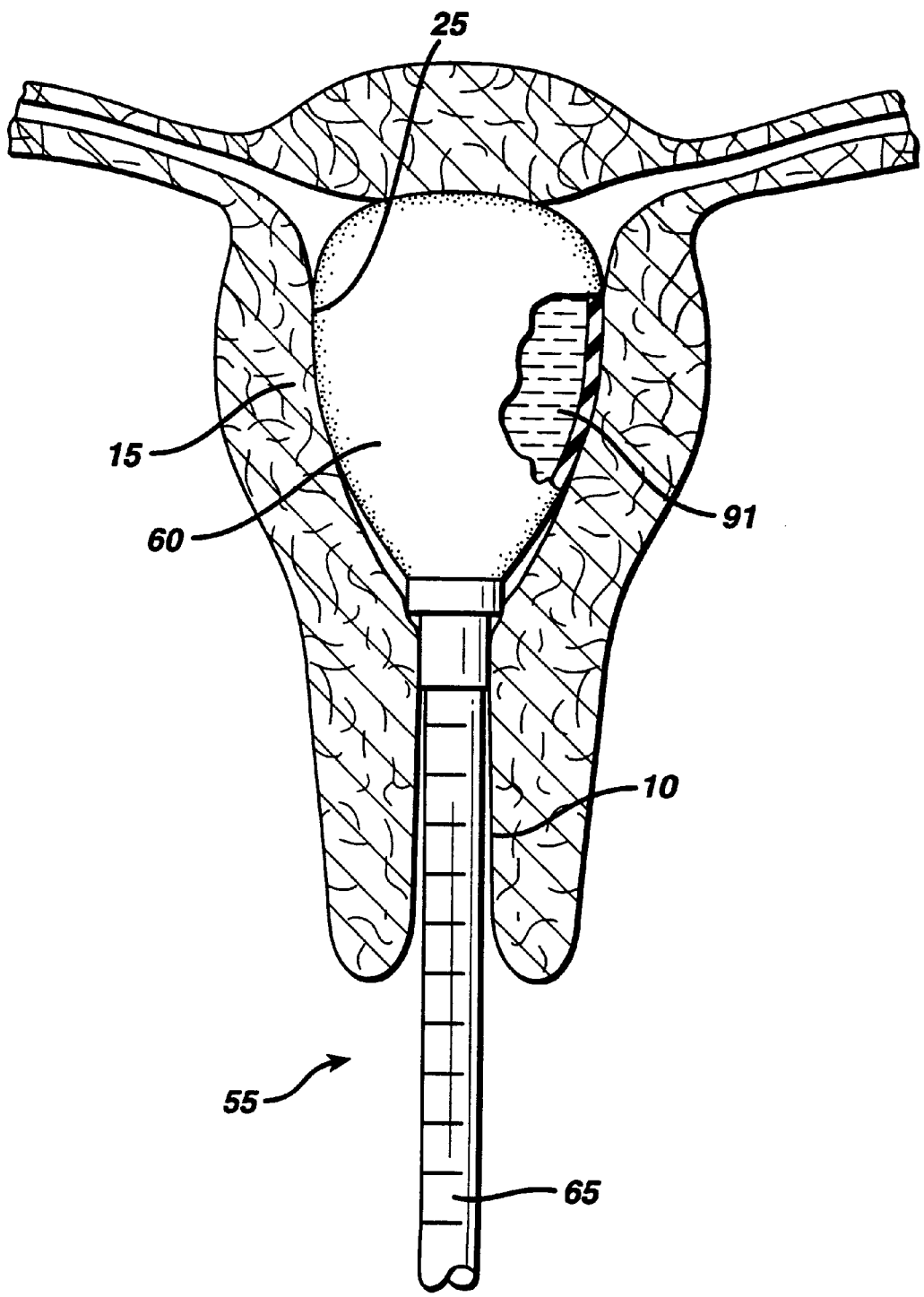
FIG. 5 illustrates the bladder of the ablation device in an inflated condition within the uterus.

Referring now to FIG. 5, a bladder 60 of apparatus 55 is shown in an inflated state within the uterus 15 and a portion of the insertion catheter 65 passing through the cervix 10. The pressure during the inflation of the bladder 60 with a physiologically compatible liquid is adjusted in such a way that the bladder contacts the endometrium 25 intimately without exerting undue force on the tissue.

FIG. 6 illustrates an embodiment of a uterine ablation apparatus 110 of the present invention. A bladder (or balloon) 155 with internal heater 160 is attached to an insertion catheter 165. A joint or articulating region 210 is provided which lets the physician articulate the catheter and pre-set an angle using a design consisting of a plurality of pleats 211. Preferably, pleats 211 are molded into the catheter 165 to form joint 165. Because bending of the catheter will produce a small amount of stretch in the wire, excess wire 215 is slidably provided for within the handle 170. The handle 170 is a conventional handle having an internal fluid passage and ports for mounting a fluid source and wires and a pressure transducer connector. The distance between the bladder 155 and the proximal end 201 of hinge 210 is preferably relatively short, such that the bendable area will be just outside of the cervix 10 (FIG. 1) Alternately, instead of making the bendable area or joint an integral part of the catheter, the catheter 165 can be made of relatively flexible material and a separate bendable slidable collar 220, made of relatively strong material, can be fabricated and slipped over the catheter just prior to use. The collar 220 will be made of a conventional material such as aluminum or thin gauge stainless steel or the like or equivalents thereof or composites of metal and polymer or polymer having sufficient yield to retain a permanent set when bent. The physician, after evaluation of the size of the uterus, can then adjust the position of the bendable site by locating the bendable collar 220 at the most desirable position and then bending the collar 220 and insertion catheter 165 to the desired degree. Being able to bend the catheter at any distance from the balloon is clearly advantageous. Inserting a bent catheter is relatively easy. As can be seen from FIG. 1, the inner diameter of the vagina 5 is considerably larger then the diameter of the cervix 10 which leads to the uterine cavity 20. As a consequence the vagina can accommodate objects of considerably larger size then the diameter of the cervical opening. Furthermore the vagina 5 is a very stretchable The vagina 5 is capable of great distension so that an ablation device, even in a fairly sharply angled configuration, can be accommodated.

FIG. 7 shows another embodiment of an apparatus 300 of the present invention in which a member or a plurality of members 325 made from a bendable material such as aluminum or tin 325 is embedded in the catheter wall 330 of catheter 365 some short distance from the bladder 355 to form joint 375. The distance would be somewhat greater then the average length of the cervix 10. The insertion catheter 365 is preferably made of stiff but bendable material so that when the physician bends the rod to the desired angle the catheter 365 resists moving back into a straight configuration. Also, insertion member 325 when bent takes a set in the bent position in joint 375. Tin or aluminum are not the only materials that can be used for members 325. Any material which dead bends is suitable including polymeric materials, composites and the like and equivalents thereof.

FIG. 8 shows still another embodiment of an apparatus 400 of the present invention. Three plate members made from a conventional memory metal 440, 445, 450 are embedded into the wall 435of the catheter 430 of apparatus 400. Each of the plates is designed so that it will curve a few degrees when warmed to a temperature at or above body temperature. Each of the plates optionally has a separate heating coil and wire 455 attached to it. The physician can then insert the ablation device 400 until the bladder 470 is just touching the cervical opening. He then presses a button on the handle (not shown) which switches power to the coils and thereby heats and curves the first plate 440 and the catheter 465 is made to bend a few degrees. If the curvature is insufficient to allow for easy entry into the cervix 10 he presses another button on the handle which activates the heater on the second plate 445 and increases the curvature of the catheter 465 more. If that is still insufficient, pressing a third button will curve the last remaining plate 450. If desired one or two plate members could be used or four or more plate members could be used. The plates could be constructed of conventional shape memory alloys such as Nitinol or equivalents thereof If desired, the material could be designed to actuate at body temperature obviating the need for individual heater coils.

FIG. 9 shows yet another embodiment of the present invention. Apparatus 500 is seen to have joint 560 joining catheter sections 566 and 567. Pins 564 extend from the proximal end of catheter 566 and are rotatably engaged in holes 571 of yoke members 570 which extend from the distal end of catheter section 567. The articulation of the catheter 565 is maintained through the use of flexible, yet locking detents 660. After examination of the relative positions of the vagina 5 and the uterus 15 in the patient, the physician can pre-set the insertion catheter 565 to an angle which is best suited to the individual situation. Although not necessary, it is possible to provide mechanisms by which the physician is able to set or alter the angle of articulation after or during insertion. One possible means of doing so is provided by pull wires 665. These wires are threaded through the retention rings 670 and eventually exit in the handle 70. Pulling on one of the two wires 665 sets an angle, pulling on the other one would then reduce the angle. In order to prevent the fluid used for inflating the bladder 555 from leaking out of the joint 560, it may be necessary—depending upon the design of the joint—to cover the joint area with a flexible rubber tube 580 which fits tightly enough to form a seal and prevent fluid from escaping.

It is clear that these examples of the invention are not the only way to achieve articulation of the insertion catheter and one skilled in the art may well find other designs which are equally suitable. The following example is illustrative of the principles and practice of the present invention although not limited thereto.

EXAMPLE

The cauterization procedure is preceded by screening against cancer of the affected region and physical condition within established norms. A PAP smear and endrometrial biopsy/curettage must exclude cancer or precancerous lesions of the uterus and cervix. If a fibroid uterus is present, an ultrasound should exclude ovarian masses. The uterine cavity must be 10 cm or less in length to be suitable for the small distensible bladder size.

It would be preferable if the patient should be post menstrual or start on Danazol, or the equivalent which causes reduction in bleeding and a thin endometrium, at a rate of 800 ml daily, from the $5^{th}$ day of the previous menstrual period until two weeks after the procedure. However, the above-mentioned is not a requirement. She will undergo the procedure in the ambulatory surgery unit or outpatient facility where Valium and/or Demerol can be given intravenously if there is pain during the heating phase of the procedure.

The apparatus of the present invention will be inserted after a bimanual examination and speculum of the cervix. Prior to insertion, the physician angulates the catheter of the device by grasping the catheter on either side of the joint and bending to the desired angle of articulation to accommodate the anatomical structure for the particular patient. Dilation to 6 mm may be required which may necessitate a local 1% lidocaine block of the cervix. Once in place the catheter stem protrudes from the vagina and consists of an electrical connecting plug, pressure line, syringe fill port, and tubing. Placement of the apparatus may be facilitated by distance markings on the catheter indicating depth of insertion.

Upon placement of the apparatus it will be connected to a control unit via attachment of the electrical connector and flexible tubing attached to the handle to their receptacles on the control unit.

Subsequent to insertion of the apparatus, the control unit will be powered on. The temperature of the fluid in the bladder will be preset to 87 degrees Celsius by the control unit and can be measured via the thermocouple located within the bladder. Fluid pressure constraints are preset and upon inflation of the distensible bladder by introduction of fluid to the fluid system by depressing the plunger on the hypodermic barrel, can be easily measured by looking at the pressure display located on the control unit.

The practitioner then process to inflate the distensible bladder by the plunger on the hypodermic barrel which may serve as the fluid source after powering up the heater in the catheter to heat the fluid to a preset temperature. The practitioner injects the fluid into the fluid system until the control unit display indicates that the fluid pressure is within the preset constraints. The volume required to fill the distensible bladder is about 30 cc in most cases in order to reach the pressure wherein the bladder is substantially in contact with all of the endometrium The heating element in the apparatus is connected via the plug to bring the fluid in the balloon to a temperature of about 87 degrees Celsius. An optional circulator in the catheter circulates fluid between the heating element and the balloon. Once that temperature level is reached, the system timer is activated to time the procedure and provide automatic turn off of the heating element at the end of a preset period.

Upon completion of the procedure, the pressure valve and plunger are depressed to allow the fluid to be withdrawn from the fluid system causing the distensible balloon to deflate. Upon deflation of the distensible balloon, the apparatus may be safely withdrawn from the patient.

The catheters of the present invention may be made of the following materials: ABS polymer, PEBAX polymer, polycarbonate, HYTREL polymer, C-FLEX polymer, or any conventional biocompatible polymeric material having sufficient rigidity and/or flexibility and thermal resistance to effectively provide the desired insertion and use properties, and equivalents thereof.

The balloons of the present invention may be made from the following materials: any biocompatible polymeric material having sufficient expandablility and thermal resistance including latex rubber, silicone rubber, polyurethane and the like and equivalents thereof.

Although this invention has been shown and described with respect to detailed embodiments thereof, it will be understood by those skilled in the art that various changes in form and detail thereof may be made without departing from the spirit and scope of the claimed invention.

We claim:

1. A uterine balloon treatment apparatus, comprising:

a catheter having a longitudinal internal passage, a distal end and a proximal end, said catheter being flexible;

a slidable collar mounted on said catheter such that when the collar is bent, the catheter is angulated;

an inflatable balloon mounted to the distal end of the catheter, said inflatable balloon having an interior, wherein the interior of the inflatable balloon is in fluid communication with the internal passage of the catheter, and a proximal end with a proximal opening and a distal end;

a handle having a hollow, longitudinal passage mounted to the proximal end of the catheter such that the interior passage of the handle is in fluid communication with the interior passage of the catheter;

a connector mounted to the handle for connecting the passage of the catheter to a source of liquid;

a heating element mounted in the internal passage of the catheter such that when said heating element is connected to a source of electrical power it generates heat; and, an electrical conductor mounted in the apparatus for providing electrical power to the heating element.

2. A method of ablating endometrial tissue form the interior of a uterus comprising the steps of:

A. providing a uterine ablation apparatus comprising:
   a catheter having a longitudinal internal passage, a distal end and a proximal end, said catheter being flexible;
   a slidable collar mounted on said catheter such that when the collar is bent, the catheter is angulated;
   an inflatable balloon mounted to the distal end of the catheter, said inflatable balloon having an interior, wherein the interior of the inflatable balloon is in fluid communication with the internal passage of the catheter, and a proximal end with a proximal opening and a distal end;
   a handle having a hollow, longitudinal passage mounted to the proximal end of the catheter such that the interior passage of the handle is in fluid communication with the interior passage of the catheter;
   a connector mounted to the handle for connecting the passage of the catheter to a source of liquid;
   a heating element mounted in the internal passage of the catheter such that when said heating element is connected to a source of electrical power it generates heat; and,
   an electrical conductor mounted in the apparatus for providing electrical power to the heating element;
B. inserting the balloon and distal end of the catheter into a uterus having an endometrial layer; and,
C. heating the endometrial layer to a sufficient temperature for a sufficient length of time to effectively ablate the layer.

3. An endometrial ablation device comprising:
a catheter having a longitudinal internal passage, a distal end and a proximal end, said catheter being flexible; and
a slidable collar mounted on said catheter such that when the collar is bent, the catheter is angulated;
a handle having a hollow, longitudinal passage mounted to the proximal end of the catheter such that the interior passage of the handle is in fluid communication with the interior passage of the catheter; and
a connector mounted to the handle for connecting the passage of the catheter to a source of liquid or gas useful for ablating the endometrium.

4. A method of ablating endometrial tissue form the interior of a uterus comprising the steps of:
   B. providing a uterine ablation apparatus comprising:
      a catheter having a longitudinal internal passage, a distal end and a proximal end, said catheter being flexible;
      a slidable collar mounted on said catheter such that when the collar is bent, the catheter is angulated;
      a handle having a hollow, longitudinal passage mounted to the proximal end of the catheter such that the interior passage of the handle is in fluid communication with the interior passage of the catheter;
      a connector mounted to the handle for connecting the passage of the catheter to a source of liquid or gas;
   B. inserting the distal end of the catheter into a uterus having an endometrial layer; and,
   C. heating or cooling the endometrial layer to a sufficient temperature for a sufficient length of time to effectively ablate the layer.

* * * * *